United States Patent [19]

Kunze

[11] Patent Number: 4,848,921
[45] Date of Patent: Jul. 18, 1989

[54] APPARATUS AND METHOD FOR POWER COMPENSATION IN A DIFFERENTIAL SCANNING CALORIMETER

[75] Inventor: Wolfgang Kunze, Rodgau, Fed. Rep. of Germany

[73] Assignee: Bodenseewerk Perkin-Elmer & Co., GmbH, Fed. Rep. of Germany

[21] Appl. No.: 909,531

[22] Filed: Sep. 22, 1986

Related U.S. Application Data

[63] Continuation of Ser. No. 857,708, May 1, 1986, abandoned.

[30] Foreign Application Priority Data

May 14, 1985 [DE] Fed. Rep. of Germany ....... 3517693

[51] Int. Cl.⁴ ............................................. G01N 25/00
[52] U.S. Cl. ......................................... 374/11; 374/31
[58] Field of Search ............................. 374/11, 31, 12

[56] References Cited

U.S. PATENT DOCUMENTS

| | | | |
|---|---|---|---|
| 3,263,484 | 8/1966 | Watson et al. | 374/11 |
| 3,675,465 | 7/1972 | Sommer et al. | 374/11 |
| 4,255,961 | 3/1981 | Biltonen et al. | 374/11 |

OTHER PUBLICATIONS

IPC #WO82/01248, Apr. 15, 1982, Publication, "Method and Apparatus for Nondestructively Determining the Composition of an Unknown Material Sample", O. H. Hammond, III, (G01N 25/00).
Analytical Chemistry, vol. 26, No. 7, Jul. 1954, pp. 1238-1240, "Quantitative Estimation of Aromatic Nitro Compounds" by E. Wolthuis et al.
Analytical Chemistry, vol. 36, No. 7, Jun. 1964, pp. 1238-1245, "The Analysis of a Temperature-Controlled Scanning Calorimeter" by M. J. O'Neill.
Chemi-Technik 5 (1976) 321-325, (pp. 1-5), Quantitative Thermo-Analyse Mit Hilfe der . . . Thermogravimetrie, by V. W. Kunze.

*Primary Examiner*—Daniel M. Tasich
*Attorney, Agent, or Firm*—Ronald G. Cummings; Edwin T. Grimes; Patrick T. Murphy

[57] ABSTRACT

Apparatus and methods are disclosed for performing power compensation in a differential scanning calorimeter. The device operates by first subjecting only a reference material, in a single furnace, to a predetermined, variable, temperature program supplied by a program control. The values of the heating power supplied to the reference material are stored in a memory as a function of the temperature measured at the single furnace by a temperature sensor. The sample is then exposed, in the same furnace, to heating powers which are consecutively applied to the furnace, under program control, in accordance with the values stored in memory. The real temperatures of the sample are then measured by the temperature sensor. A supplementary compensating heating power is supplied to the sample, which power varies in accordance with the difference between the stored, programmed temperature and the real temperature in the sense of eliminating this temperature difference. This supplementary compensating heating power is then outputted to and registered, respectively, at an output device such as a recorded or computer.

6 Claims, 1 Drawing Sheet

APPARATUS AND METHOD FOR POWER COMPENSATION IN A DIFFERENTIAL SCANNING CALORIMETER

This application is a continuation of U.S. Ser. No. 857,708 filed May 1, 1986, now abandoned.

BACKGROUND OF THE INVENTION

1. Field of the Invention

The invention relates generally to thermal analysis and, more particularly, to differential thermal analysis performed by using a scanning calorimeter.

2. Description of the Relevant Art

Differential thermal analysis is an old and well-known method for the analysis of materials. Basically, the method consists of simultaneously applying heat to a sample material and a reference material. As the sample material goes through various physical and chemical changes, such as crystallization, melting, freezing, oxidation, etc., its temperature is affected by the changes in internal energy. The differences in temperature between the sample and reference are recorded and, from this data, calculations may be made for determing the internal energy changes occurring in the sample.

One such method, and the apparatus to implement it, is disclosed in U.S. Pat. No. 3,263,484 issued Aug. 2, 1966 to Watson, et al, assigned to the Perkin-Elmer Corporation of Norwalk, Conn. U.S. Pat. No. 3,263,484 is hereby incorporated by reference.

The referenced patent teaches both apparatus and methods for performing dynamic power difference calorimetry, where; (a) a sample and a reference are subjected to a predetermined temperature program; (b) the heating powers supplied to the sample and the reference are varied, one related to the other, as a function of the temperature differences between sample and reference to eliminate the temperature differences; and (c) the difference of these heating powers, supplied to the sample and the reference, is then provided as output.

U.S. Pat. No. 3,263,484 goes on to teach that when a sample is subjected to a temperature program, for example a temperature increased linearly with respect to time, endothermic or exothermic transformations may ocur in such a sample whereby energy is consumed or energy is supplied. This may concern physical transformations such as melting, but also, for example, chemical reactions.

The determnation of the points at which these transformations occur may give information about the type of sample being analyzed. In order to measure this transformation heat, in the arrangement of the prior art, a sample and a reference are each arranged on a heatable plate such that heating energy may be supplied to the sample and the reference separately and independently of each other. One temperature sensor is arranged at the sample and another at the reference.

A program control makes sure that the average value of the temperatures of sample and reference follows a predetermined temperature program. Furthermore, a control system is provided which eliminates the temperature difference between sample and reference by asymmetrically supplying heating energy to the sample and the reference.

A measuring device is provided, which converts the difference of the heating powers supplied to the sample and to the reference, into a voltage difference, which is then recorded as a measure of the transformation heats of the sample.

Similar methods and apparatus are described in "Analytical Chemistry", 36 (1964), page 1233 to 1238, and in "Analytical Chemistry 26 (1964), page 1238 to 1245.

Further yet, a method for quantitative thermal analysis with a differential calorimeter is described in "Chemie-Technik" 5 (1976) page 321 to 325. In this arrangement a sample and a reference are also arranged in two different separately heatable furnaces. A program pickup controls, through a program amplifier, the heaters of the furnaces for the sample and reference. A temperature sensor which responds to the temperature of the sample and of the reference, respectively, is arranged at each of the two furnaces. The differences of these two temperatures control through a "T amplifier", a heating power amplifier which is arranged to apply compensating heat to the sample and the reference such that the temperature difference is eliminated. A recorder uses, as abscissa, the temperature predetermined by the temperature pickup, and as ordinate, the compensating heat supplied by the heating power amplifier.

The aforesaid methods and devices of the prior art require two furnaces. An extremely high technical expenditure is required for adjusting the two furnaces exactly enough such that an exactly reproducible relation is ensured between the difference of the heating powers supplied to the sample and the reference, and the real energy consumption (or supply) of the sample. The two furnaces with the associated adjusting and controlling means constitute a further considerable expenditure in construction cost.

Accordingly, it would be desirable to have apparatus and methods for performing power compensation in a differential scanning calorimeter which eliminates the problems associated with the prior art.

SUMMARY OF THE INVENTION

According to the invention, apparatus and methods are disclosed for performing power compensation in a differential scanning calorimeter that employs only a single furnace. First, only a reference is subjected, in the single furnace, to a predetermined, variable, temperature program supplied by temperature program control means. The values of the heating power supplied to the reference are stored in a memory as a function of the temperature measured at the single furnace by a temperature sensor.

The sample is then exposed, in the same furnace, to heating powers which are consecutively applied to the furnace, under program control, in accordance with the values stored in memory. The real temperatures of the sample are then measured by the temperature sensor. A supplementary compensating heating power is supplied to the sample, which power varies in accordance with the difference between the stored, programmed temperature and the real temperature in the sense of eliminating this temperature difference. This supplementary compensating heating power is then output and registered, respectively, at an output device such as a recorder or computer.

It is an object of the invention to provide apparatus and methods for performing power compensation in a differential scanning calorimeter using only a single furnace in which accurately reproducible conditions may be established.

It is a further object of the invention to provide apparatus and methods for performing power compensation in a differential scanning calorimeter which subject samples and reference materials to temperature programs under reproducible conditions without having to make the supplementary adjustments required by known calorimeters which are two furnace devices.

It is still a further object of the invention to provide apparatus and methods for performing power compensation in a differential scanning calorimeter which costs less to construct and which is more reliable than conventional differential scanning calorimeters.

There has thus been outlined, rather broadly, the more important objects of the invention in order that the detailed description thereof that follows may be better understood, and in order that the present contribution to the art may be better appreciated. There are, of course, additional objects and features of the invention that will be described more fully hereinafter. Those skilled in the art will appreciate that the conception on which this disclosure is based may readily be utilized as the basis of the designing of other apparatus for carrying out the various purposes of the invention. It is important, therefore, that this disclosure be regarded as including such equivalent apparatus as do not depart from the spirit and scope of the invention.

One embodiment of the invention has been chosen for purposes of illustration and description, and is shown in the accompanying Drawing forming a part of the specification.

DETAILED DESCRIPTION

Figure 1:
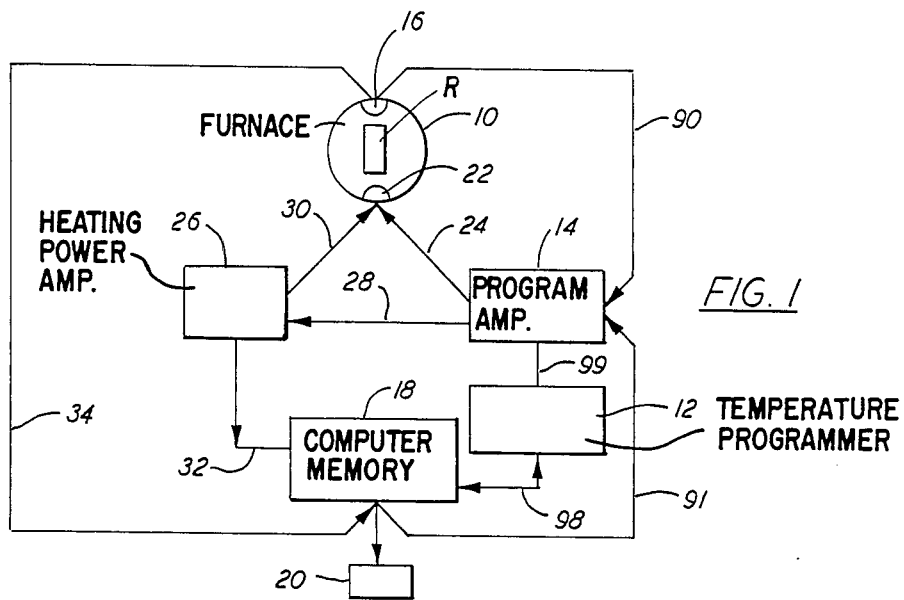
FIG. 1 shows a device for performing the dynamic power difference calorimetry during a zero run of a reference.

With reference to FIG. 1 it may be seen that the novel device comprises a single furnace 10 into which a sample to be analyzed or a reference may be optionally inserted. The furnace 10 is arranged to consecutively receive sample and reference. If required the device may be operated with only furnace 10 as a reference although a reference material R is shown in FIG. 1.

The novel device is further comprised of temperature program means 12 which determines a temperature program, that is a certain course of the desired temperature as a function of time. This desired temperature value is applied, via link 99, to program amplifier 14. The device also includes temperature sensor 16, shown in FIG. 1 to be associated with furnace 10, which responds to the temperature of the sample or the reference in said furnace.

Temperature program means 12 supplies the desired temperature values to computer memory 18 via link 98. Computer memory 18, in turn, supplies the desired temperature values to output 20. The real temperature supplied by temperature sensor 16 and the desired temperature at output 20, are applied to program amplifier 14 via links 90 and 91 respectively. The average value of these two temperatures is formed and compared at amplifier 14 to the desired temperature value provided to amplifier 14 by means 12 via link 99 as described hereinbefore.

Heater 22 of furnace 10 is shown in FIG. 1 to be controlled by program amplifier 14. Control is effected as a function of the deviation between programmed desired temperature value and said average value, such that the average value follows the program predetermined by means 12. This is illustrated in FIG. 1 by the arrow 24.

A heating power amplifier 26 may be controlled by the difference of the real temperature at sensor 16 and the desired temperature value at output 20, as illustrated in FIG. 1 by arrow 28.

The heating power amplifier controls a compensating heating power of heater 22 by which said difference between the real temperature and the desired temperature value is made zero. This is illustrated in FIG. 1 by arrow 30.

The preferred embodiment of the disclosed service may be similar to the device shown in the U.S. Pat. No. 3,263,484, previously incorporated herein by reference, if the sample and reference temperature described therein is replaced by the reference temperature and the desired temperature value referred to hereinbefore.

The compensating heat applied by heating power amplifier 26 is supplied to computer memory 18 through input 32. Simultaneously computer memory 18 receives, via conductor 34, the corresponding real temperature at temperature sensor 16. The compensating heating power and the corresponding temperatures are read-in into computer memory 18, the temperatures assuming the function of the addresses for the compensating heating powers.

Figure 2:
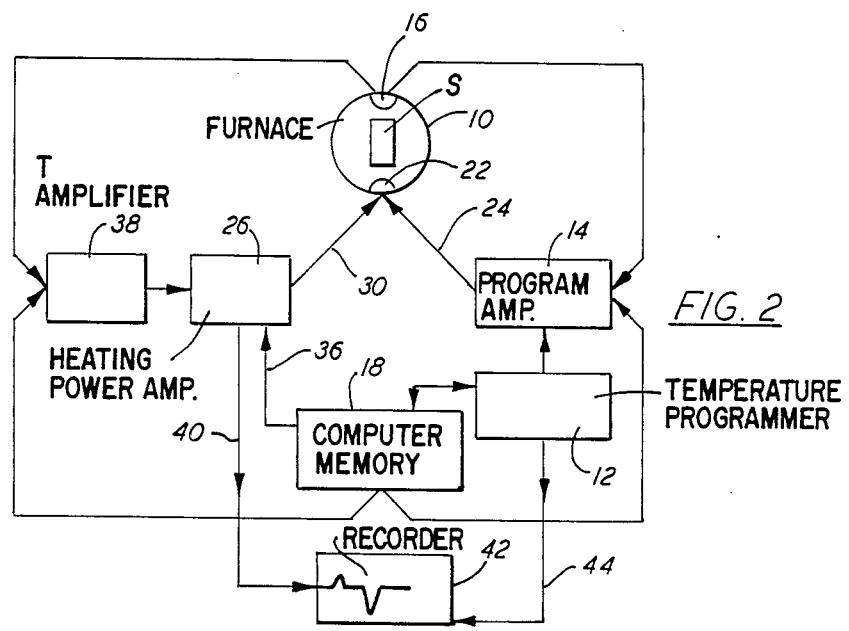
FIG. 2 shows the device at the measuring run with a sample to be analyzed.

FIG. 2 shows the subsequent measurement with a samples.

Means 12 supplies a desired temperature value for program amplifier 14. Simultaneously, means 12 controls computer memory 18 and interrogates the compensating heating power which has been associated when measuring the reference of the respective desired temperature value. This value of the compensating heating temperature is applied to heating power amplifier 26, as illustrated by the arrow 36.

Program amplifier 14 receives, on one hand, the desired value temperature and forms the average value of the real sample temperature measured by temperature sensor 16, and of the reference temperature supplied by computer memory 18 and associated with the value of the compensating heating power on line 36. In accordance with arrow 24 of FIG. 2, program amplifier 14 controls heater 22, such that this average value is equal to the desired temperature value predetermined by means 12. Simultaneously, the reference temperature is applied to T amplifier 38 by computer memory 18, and the sample temperature is applied to amplifier 38 by temperature sensor 16. T amplifier 38 controls heating power amplifier 26, such that by accordingly varying the compensating heating power, the real sample temperature is caused to follow the reference temperature from computer memory 18.

The compensating heating power is applied as ordinate, by the heating power amplifier 26, through line 40 to a recorder 42. The desired temperature value, supplied by means 12, serves as abscissa of recorder 42, as indicated by the line 44.

Thus, what has been disclosed are both apparatus and methods for consecutively subjecting a sample and a reference to a temperature program under the same conditions in a single furnace, avoiding the supplementary adjustments required by prior art devices and achieving the other objects of the invention set forth hereinbefore.

The foregoing description of a preferred embodiment of the novel device and methods for achieving the objects of the invention has been presented for the purposes of illustration and description only. It is not intended to be exhaustive or to limit the invention to the precise form disclosed, and obviously many modifications and variations are possible in light of the above teaching. The embodiment was chosen and described in order to best explain the principles of the instant invention and its practical application to thereby enable others skilled in the art to best utilize the instant invention in various embodiments and with various modifications as are suited to the particular use contemplated. It is intended that the scope of the instant invention be defined by the claims appended hereto.

What is claimed is:

1. A method for performing power compensation in a differential scanning calorimeter, comprising the steps of:
   subjecting consecutively, in a single furnace, a sample and a reference to a predetermined temperature program, said subjecting being performed first only on said reference;
   varying the heating powers supplied to said sample and said reference, one relative to the other, as a function of the temperature differences, if any, between said sample and said reference to eliminate any such temperature difference;
   storing values of the heating power supplied to said reference, as a function of temperature measured at said furnace, in a storage device; and
   outputting a signal indicative of the difference of the heating powers supplied to said sample and said reference.

2. A method for performing power compensation in a differential scanning calorimeter, comprising the steps of:
   subjecting consecutively, in a single furnace, a sample and a reference to a predetermined temperature program, said subjecting being performed first only on said reference;
   varying the heating powers supplied to said sample and said reference, one relative to the other, as a function of the temperature differences, if any, between said sample and said reference to eliminate any such temperature difference; storing values of the heating power supplied to said reference, as a function of temperature measured at said furnace, in a storage device;
   exposing said sample, in the same furnace in which said reference was subjected to said predetermined temperature program, to heating powers corresponding to said stored heating power values; and
   outputting a signal indicative of the difference of the heating powers supplied to said sample and said reference.

3. Apparatus for performing power compensation in a differential scanning calorimeter, comprising:
   means for varying the temperature of a sample and a reference, in accordance with a predetermined temperature program, wherein said means for varying temperature further comprises a single furnace arranged to consecutively receive said sample and said reference and temperature program control means which is operative to vary the heating power supplied to said single furnace in accordance with said predetermined program;
   means for varying the heating power supplied to said sample and said reference, relative to each other, as a function of the temperature difference between said sample and said reference, to eliminate the temperature difference therebetween;
   means for outputting a measure of the difference of the heating powers supplied to said sample and said reference;
   temperature sensing means, associated with said single furnace, for measuring the temperature of said sample and said reference, respectively;
   storage means, arranged to store the values of the heating powers supplied to said furnace when containing said reference, as a function of the temperatures measured by said temperature sensing means, said storage means further comprises a memory, the contents of which are applied to said program control means which in turn consecutively applies said heating powers to said furnace in accordance with the values stored in said memory; and
   said means for varying the heating power supplied to said sample and said reference further comprises a control system to which the difference of the real temperature of said sample measured by said temperature sensor and a temperature stored in said memory, associated with a predetermined heating power, is applied as input and wherein said control system is responsive to said input to vary a supplementary compensating heating power of said sample to eliminate any such difference.

4. Apparatus as set forth in claim 1 wherein said means for outputting further comprises means for measuring and outputting an indication of the value of said compensating heating power.

5. A method for performing power compensation in a differential scanning calorimeter, comprising the steps of:
   subjecting consecutively, in a single furnace, a sample and a reference to a predetermined temperature program, said subjecting being performed first only on said reference;
   varying the heating powers supplied to said sample and said reference, one relative to the other, as a function of the temperature differences, if any, between said sample and said reference to eliminate any such temperature difference;
   storing values of the heating power supplied to said reference, as a function of temperature measured at said furnace, in a storage device;
   exposing said sample, in the same furnace in which said reference was subjected to said predetermined temperature program, to heating powers corresponding to said stored heating power values;
   measuring real temperature of said sample;
   supplying a supplementary compensating heating power to said sample;
   varying said compensating heating power in accordance with the difference between a stored programmed temperature value and the corresponding real temperature value measured, to eliminate any difference therebetween;
   outputting a signal indicative of the difference of the heating powers supplied to said sample and said reference; and
   measuring and outputting said supplementary compensating heating power.

6. Apparatus for performing power compensation in a differential scanning calorimeter, comprising:

means for varying the temperature of a sample and a reference, in accordance with a predetermined temperature program, wherein said means for varying temperature further comprises a single furnace arranged to consecutively receive said sample and said reference and temperature program control means which is operative to vary the heating power supplied to said single furnace in accordance with said predetermined program;

means for varying the heating power supplied to said sample and said reference, relative to each other, as a function of the temperature difference between said sample and said reference, to eliminate the temperature difference therebetween;

means for outputting a measure of the difference of the heating powers supplied to said sample and said reference;

temperature sensing means, associated with said single furnace, for measuring the temperature of said sample and said reference, respectively; and storage means, arranged to store the values of the heating powers supplied to said furnace when containing said reference, as a function of the temperatures measured by said temperature sensing means, said storage means further comprises a memory, the contents of which are applied to said program control means which in turn consecutively applies said heating powers to said furnace in accordance with the values stored in said memory.

* * * * *